United States Patent [19]

Murib et al.

[11] Patent Number: 4,888,443

[45] Date of Patent: Dec. 19, 1989

[54] PROCESS FOR THE PRODUCTION OF PIMELIC ACID

[75] Inventors: Jawad H. Murib, Cincinnati; John H. Kahn, Wyoming, both of Ohio

[73] Assignee: National Distillers and Chemical Corporation, New York, N.Y.

[21] Appl. No.: 659,466

[22] Filed: Oct. 9, 1984

[51] Int. Cl.$^4$ .................. C07C 51/12; C07C 55/16
[52] U.S. Cl. .................... 562/517; 562/590; 562/602
[58] Field of Search ........................... 562/517

[56] References Cited

U.S. PATENT DOCUMENTS 3,509,209  4/1970  Fenton ........................ 562/517

Primary Examiner—Vivian Garner
Attorney, Agent, or Firm—Kenneth D. Tremain; Gerald A. Baracka

[57] ABSTRACT

A process for the production of pimelic acid comprising reacting $\epsilon$-caprolactone with carbon monoxide and water in the presence of a carbonylation catalyst, such as a Group VIII metal and hydrogen halide.

7 Claims, No Drawings

PROCESS FOR THE PRODUCTION OF PIMELIC ACID

BACKGROUND OF THE INVENTION

This invention relates to a process for the production of pimelic acid and more particularly to a process for the production of pimelic acid from ε-caprolactone.

Pimelic acid (heptanedioic acid) and derivatives thereof are useful chemical compounds. For example, pimelic acid may be employed in the synthesis and manufacture of plasticizer esters, polyamides, alkyl resins, polyesters, polyurethanes, elastomers and a wide variety of other useful products, such as stabilizers, curing agents, lubricants and greases, fuel additives, adhesives and binders, paints, varnishes, corrosion inhibitors, soaps, detergents, bleaches and textiles.

More particularly and for example, pimelic acid copolymerizes with 1,5-pentanediamine to form Nylon 5,7. Recent research indicates that this odd Nylon (having an odd number of carbon atoms in each monomer unit) can be electrically active and may have potential as a conducting polymer. For example, see G. Froyer et al. J. Polymer Science, Polymer Chem. Ed., 19, 165–174 (1981).

Present electronic devices and electrically active materials are comprised of metals, semimetals, ceramics and other inorganic substances. In many applications, their utility is restricted by excess weight, mechanical fragility, fabrication problems, corrosion, scarcity and high cost. Thus, there has been a considerable interest in replacing these metals and inorganics with conducting polymers such as the afore-said Nylon.

Use of pimelic acid, however, in meeting this need to provide conducting polymers, for example, is limited by the high cost of its production. Known syntheses for pimelic acid include the non-selective oxidation of expensive starting materials, such as cycloheptanone, 1,7-heptanediol, 1,5-dicyanopentane or ricinoleic acid. U.S. Patents which disclose some syntheses for pimelic acid include U.S. Pat. No. 2,800,507, U.S. Pat. No. 2,826,609, U.S. Pat. No. 3,600,420, U.S. Pat. No. 2,698,339, U.S. Pat. No. 2,826,609 and U.S. Pat. No. 2,800,507.

A particularly interesting synthesis for the preparation o dicarboxylic acids and particularly pimelic acid, is disclosed in Japanese Patent No. 79-92913. This synthesis involves reacting lactones with carbon monoxide in the presence of a platinum group compound, such as a rhodium compound, as a catalyst, and an iodine compound, such as methyl iodide, as a promoter. Moreover, this Japanese patent discloses other prior art syntheses of dicarboxylic acids which involve the carbonylation of lactones including γ-valerolactone, γ-butyrolactone, or -δ-valerolactone in the presence of an iodine compound and a nickel or cobalt compound under high pressures and temperatures.

U.S. patents which disclose the preparation of dicarboxylic acids from lactones include U.S. Pat. No. 2,449,987, U.S. Pat. N. 2,444,988, U.S. Pat. No. 3,849,457 and U.S. Pat. No. 3,342,838.

The use of ε-caprolactone as a starting material in the preparation of pimelic acid offers a selective and potentially economic route for its preparation. However, improved synthetic methods which provide pimelic acid more selectively and in higher yields are desired if the applications of this dibasic acid are to be expanded as indicated hereinabove.

SUMMARY OF THE INVENTION

Accordingly, it is one objective of the present invention to provide an improved process for the production of pimelic acid which is economic, selective and provides the desired product in good yield.

This and other objectives are accomplished herein by a process for the preparation of pimelic acid, said process comprising reacting ε-caprolactone with carbon monoxide and water in the presence of a carbonylation catalyst and a hydrogen halide promoter.

DETAILED DESCRIPTION OF THE INVENTION

In accordance with the present invention, pimelic acid is prepared by the reaction of ε-caprolactone with carbon monoxide and water in the presence of a carbonylation catalyst such as a Group VIII metal as a heterogeneous catalyst and a hydrogen halide as a promoter.

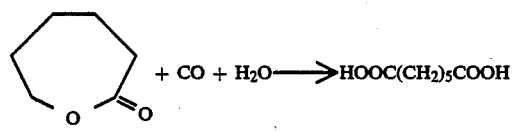

While not wishing to be bound by theory, the mechanism for the reaction of the present invention is envisioned as follows, wherein the Group VIII metal is palladium and the hydrogen halide is HI:

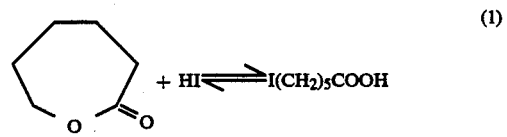

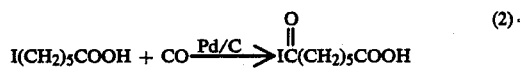

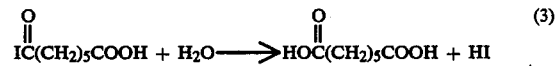

Water is present in the process of the invention in at least stoichiometric amounts with respect to the starting lactone. Thus, for example, the molar ratio of water to starting lactone may vary in a range of from about 1:1 to about 30:1, respectively. In this regard, it has been suprisingly found herein that the utilization of water in excess of the required stoichiometric molar ratio of water to lactone improves the yield of pimelic acid by retarding the formation of polymeric by-products. Thus, the preferred molar ratio of water to lactone is from about 5:1 to about 15:1.

Group VIII metals useful as catalysts herein, include, for example, palladium, platinum, ruthenium, nickel and cobalt, supported or unsupported.

Useful hydrogen halide promoters include, for example, HCl, HBr, HI and mixtures thereof. HI is the preferred promoter. Co-promoters, such as As(Ph)₃, P(Ph)₃, Sb(Ph)₃, Bi(Ph)₃, (wherein Ph=phenyl) and the like may also be used in conjunction with the hydrogen halide promoter.

The quantities of reagents, solvents, catalysts and promoters used in the present process for the production of pimelic acid vary within wide ranges. The molar ratio of Group VIII metal to hydrogen halide promoter used is, for example, from about 1:10 to about 1:100.

The molar ratio of ε-caprolactone to catalyst employed ranges, for example, from about 150:1 to about 500:1.

The process of the present invention may or may not be carried out in the presence of a solvent such as an alcohol, e.g., methanol; carboxylic acid, such as acetic acid; aromatic or aliphatic hydrocarbon; and the like.

Carbon monoxide is used at pressures of from about 600 to about 3000 psig.

The reaction is carried out at elevated temperatures and preferably at temperatures from about 175° to about 225° C.

The following examples are offered by way of illustration.

EXAMPLE 1

A 70 ml Hastelloy pressure reactor with glass liner is charged with 0.5 g 5% Pd/C, 5 ml (40 mmoles) ε-caprolactone, 5 ml (278 mmoles) $H_2O$ and 1 ml 57% aqueous hydriodic acid (6.5 mmoles HI). The reactor is flushed and pressurized with CO to 2500 psig, sealed and heated with shaking at 200° C. for 6 hours. After cooling, the reactor is vented slowly. The solid mass in the glass liner is dissolved in acetone, the reactor washed with acetone and the combined solution filtered to remove the supported catalyst. The filter paper and additional acetone are then placed into a 50 ml round bottom flask connected to a water-cooled condenser and heated under reflux for several hours to solubilize residual $C_7$ dibasic acid not soluble in cold acetone. The acetone solutions are combined and made to volume in a 50 ml volumetric flask.

Analysis of the reaction mixture shows that 98.9% of the ε-caprolactone is converted with selectivities of 49.2% pimelic acid, 36.6% branched $C_7$-dibasic acids, and 11.1% hexanoic acid. The components are analyzed by gas chromatography (as their methyl esters) and their identification confirmed by their mass and NMR spectra.

EXAMPLE 2

The procedure of Example 1 is repeated except that 8 ml (133 mM) acetic acid is employed as solvent instead of water and the amount of ε-caprolactone is 2 ml rather than 5 ml. Analysis of the reaction mixture shows that pimelic acid is present.

EXAMPLES 3–12

The procedure of Example 1 is followed to further illustrate the effects of different amounts of water, catalyst, and promoter, as well as various temperatures on the product distribution.

The results are given in Table 1.

TABLE 1

| sample | mM ε-caprolactone | mM $H_2O$ | mM HI | Temp., °C. | 5% Pd/C,g. | Conv., % | % Selectivity Pimelic Acid | Other $C_7$ Acids | Hexanoic Acid | γ-caprolactone | Polymer |
|---|---|---|---|---|---|---|---|---|---|---|---|
| 1 | 40 | 322 | 6.5 | 200 | 0.5 | 98.9 | 49.2 | 36.2 | — | — | — |
| 2 | 16 | 44[1] | 6.5 | 200 | 0.5 | — | present | — | — | — | — |
| 3 | 40 | 44 | 6.5 | 200 | 0.5 | 92.2 | 22.6 | — | — | — | present |
| 4 | 40 | 99 | 6.5 | 200 | 0.5 | >90 | 30.7 | — | — | — | present |
| 5 | 40 | 322 | 6.5 | 200 | 0.5 | 96.5 | 46.7 | 33.6 | 18.4 | — | none |
| 6 | 40 | 599 | 6.5 | 200 | 0.5 | 93.2 | 41.5 | 43.7 | 13.9 | — | none |
| 7 | 40 | 282 | 0.7 | 225 | 0.5 | 56.4 | 16.8 | 20.1 | 0.7 | 40.3 | — |
| 8 | 40 | 388 | 16.3 | 200 | 0.5 | 98.4 | 40.4 | 34.4 | 14.5 | 1.8 | — |
| 9 | 40 | 322 | 6.5 | 200 | 0.25 | 79.9 | 43.6 | 37.1 | 5.5 | 8.7 | — |
| 10 | 40 | 322 | 6.5 | 175 | 0.5 | 41.1 | 40.4 | 31.6 | 2.8 | — | none |
| 11 | 40 | 322 | 6.5 | 225 | 0.5 | 98.3 | 40.5 | 36.4 | 17.0 | — | none |
| 12 | 40 | 599 | 6.5 | 175 | 0.5 | 20.3 | 44.8 | 52.2 | 3.0 | — | none |

[1] Acetic acid is used as solvent in place of water.

Obviously, other modifications and variations of the present invention are possible in light of the above teachings. It is therefore to be understood that changes may be made in the particular embodiments of this invention which are within the full intended scope of the invention as defined by the appended claims.

What is claimed is:

1. A process for the preparation of pimelic acid, said process comprising reacting ε-caprolactone with carbon monoxide and water in the presence of a carbonylation catalyst and a hydrogen halide, the molar ratio of water to ε-caprolactone being from about 5:1 to 15:1 to retard formation of polymeric by-products.

2. The process of claim 1 wherein said hydrogen halide is hydrogen iodide.

3. The process of claim 1 wherein said reaction is carried out at a temperature in the range of from about 175° to about 225° C.

4. The process of claim 1 wherein said carbonylation catalyst is a Group VIII metal.

5. The process of claim 4 wherein said Group VIII metal is selected from the group consisting of palladium, platinum, ruthenium, nickel and cobalt.

6. The process of claim 5 wherein said Group VIII metal is palladium.

7. The process of claim 6 wherein said palladium is supported on carbon.

* * * * *